United States Patent
Fathi et al.

(10) Patent No.: US 11,058,671 B2
(45) Date of Patent: *Jul. 13, 2021

(54) FORMULATIONS AND METHODS OF MANUFACTURING FORMULATIONS FOR USE IN COLONIC EVACUATION

(71) Applicant: RedHill Biopharma Ltd., Tel-Aviv (IL)

(72) Inventors: Reza Fathi, Raleigh, NC (US); Patrick Laughlin Mclean, Raleigh, NC (US)

(73) Assignee: RedHill Biopharma Ltd., Tel-Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/663,652

(22) Filed: Oct. 25, 2019

(65) Prior Publication Data

US 2020/0222375 A1 Jul. 16, 2020

Related U.S. Application Data

(63) Continuation of application No. 16/189,847, filed on Nov. 13, 2018, now Pat. No. 10,493,065, which is a continuation of application No. 14/417,172, filed as application No. PCT/IB2013/001640 on Jul. 26, 2013, now Pat. No. 10,166,219.

(60) Provisional application No. 61/676,608, filed on Jul. 27, 2012.

(51) Int. Cl.

| | |
|---|---|
| *A61K 31/4402* | (2006.01) |
| *A61K 9/20* | (2006.01) |
| *A61K 31/185* | (2006.01) |
| *A61K 31/375* | (2006.01) |
| *A61K 33/08* | (2006.01) |
| *A61K 9/28* | (2006.01) |
| *A61P 1/10* | (2006.01) |

(52) U.S. Cl.
CPC ........ *A61K 31/4402* (2013.01); *A61K 9/2009* (2013.01); *A61K 9/2013* (2013.01); *A61K 9/2095* (2013.01); *A61K 9/28* (2013.01); *A61K 9/2893* (2013.01); *A61K 31/185* (2013.01); *A61K 31/375* (2013.01); *A61K 33/08* (2013.01); *A61P 1/10* (2018.01)

(58) Field of Classification Search
None
See application file for complete search history.

(56) References Cited

U.S. PATENT DOCUMENTS

| | | | | |
|---|---|---|---|---|
| 5,843,477 | A * | 12/1998 | Alexander | A61K 9/0007 424/466 |
| 6,132,767 | A * | 10/2000 | Borody | A61K 31/44 424/456 |
| 6,475,510 | B1 * | 11/2002 | Venkatesh | A61K 9/0056 424/441 |
| 10,166,219 | B2 * | 1/2019 | Fathi | A61K 9/2009 |
| 10,493,065 | B2 * | 12/2019 | Fathi | A61P 1/10 |
| 2012/0156261 | A1 * | 6/2012 | Fujiwara | A61K 31/616 424/400 |

FOREIGN PATENT DOCUMENTS

WO    WO-2011019045 A1 *    2/2011    ........... A61K 9/0056

OTHER PUBLICATIONS

Parra-Blanco. World J Gastroenterol Dec. 21, 2014; 20(47): 17709-17726. (Year: 2014).*

* cited by examiner

*Primary Examiner* — Michael P Cohen
(74) *Attorney, Agent, or Firm* — Greenberg Traurig, LLP

(57) ABSTRACT

Formulations and methods of manufacturing formulations for use in colonic evacuation are disclosed herein, in an embodiment, a solid dosage formulation includes an intra-granular fraction intermingled with an extra-granular fraction, wherein the intra-granular fraction includes granules comprising at least one osmotic evacuant agent, at least one antacid, and a first pharmaceutically acceptable excipient component, and wherein the extra-granular fraction includes one or more organic acids, a non-metallic lubricating element, and a second pharmaceutically acceptable excipient component.

10 Claims, 2 Drawing Sheets

FORMULATIONS AND METHODS OF MANUFACTURING FORMULATIONS FOR USE IN COLONIC EVACUATION

RELATED APPLICATION

This Application is a Continuation Application of U.S. application Ser. No. 16/189,847, filed on Nov. 13, 2018 and issued as U.S. Pat. No. 10,493,065 on Dec. 3, 2019, which is a Continuation Application of U.S. application Ser. No. 14/417,172, filed on Jan. 26, 2015 and issued as U.S. Pat. No. 10,166,219 on Jan. 1, 2019, which is a National Stage Application of International Application No. PCT/IB2013/001640, filed on Jul. 26, 2013, which claims the benefit of U.S. Provisional Application No. 61/676,608, filed on Jul. 27, 2012. The entire contents of these applications are incorporated herein by reference in their entireties.

BACKGROUND

The advent of colonoscopy brought with it the need for a simplified, routine bowel cleansing protocol or product to achieve a clean colonic mucosa required to detect even small lesions or abnormalities in the bowel. Similar requirements exist for colonic surgery.

SUMMARY

Formulations and methods of manufacturing formulations for use in colonic evacuation are disclosed herein.

According to aspects illustrated herein, there is disclosed a solid dosage formulation that includes an intra-granular fraction intermingled with an extra-granular fraction, wherein the intra-granular fraction includes granules comprising at least one osmotic evacuant agent, at least one antacid, and a first pharmaceutically acceptable excipient component, and wherein the extra-granular fraction includes one or more organic acids, a non-metallic lubricating element, and a second pharmaceutically acceptable excipient component.

According to aspects illustrated herein, there is disclosed a method of evacuating a colon of a patient that includes orally administering to the patient, within a 24-hour time frame, between 25 and 30 tablets with a liquid, wherein each of the tablets includes an intra-granular fraction intermingled with an extra-granular fraction, wherein the intra-granular fraction includes granules comprising sodium picosulfate, magnesium oxide, simethicone and a first pharmaceutically acceptable excipient component, wherein the extra-granular fraction includes ascorbic acid and a second pharmaceutically acceptable excipient component, and wherein all the tablets combined yield a total dose of about 30 mg sodium picosulfate, about 7 g of magnesium oxide, about 15 g of ascorbic acid, and about 100 mg of simethicone. In an embodiment, the formulation requires a minimum ingestion of fluid while avoiding side effects of fluid shifts. In an embodiment, the formulation has an optimal drug release profile and suitable stability to provide adequate shelf life.

According to aspects illustrated herein, there is disclosed a method of manufacturing a solid dosage formulation that includes (i) wet granulating at least one osmotic evacuant agent, at least one antacid, and a first pharmaceutically acceptable excipient component to form an intra-granular fraction; (ii) blending the intra-granular fraction obtained from step (i) with elements of an extra-granular fraction comprising one or more organic acids, a non-metallic lubricating element, and a second pharmaceutically acceptable excipient component; and (iii) compressing the blend obtained from step (ii) into tablets.

BRIEF DESCRIPTION OF THE DRAWINGS

The presently disclosed embodiments will be further explained with reference to the attached drawings.

Figure 1:
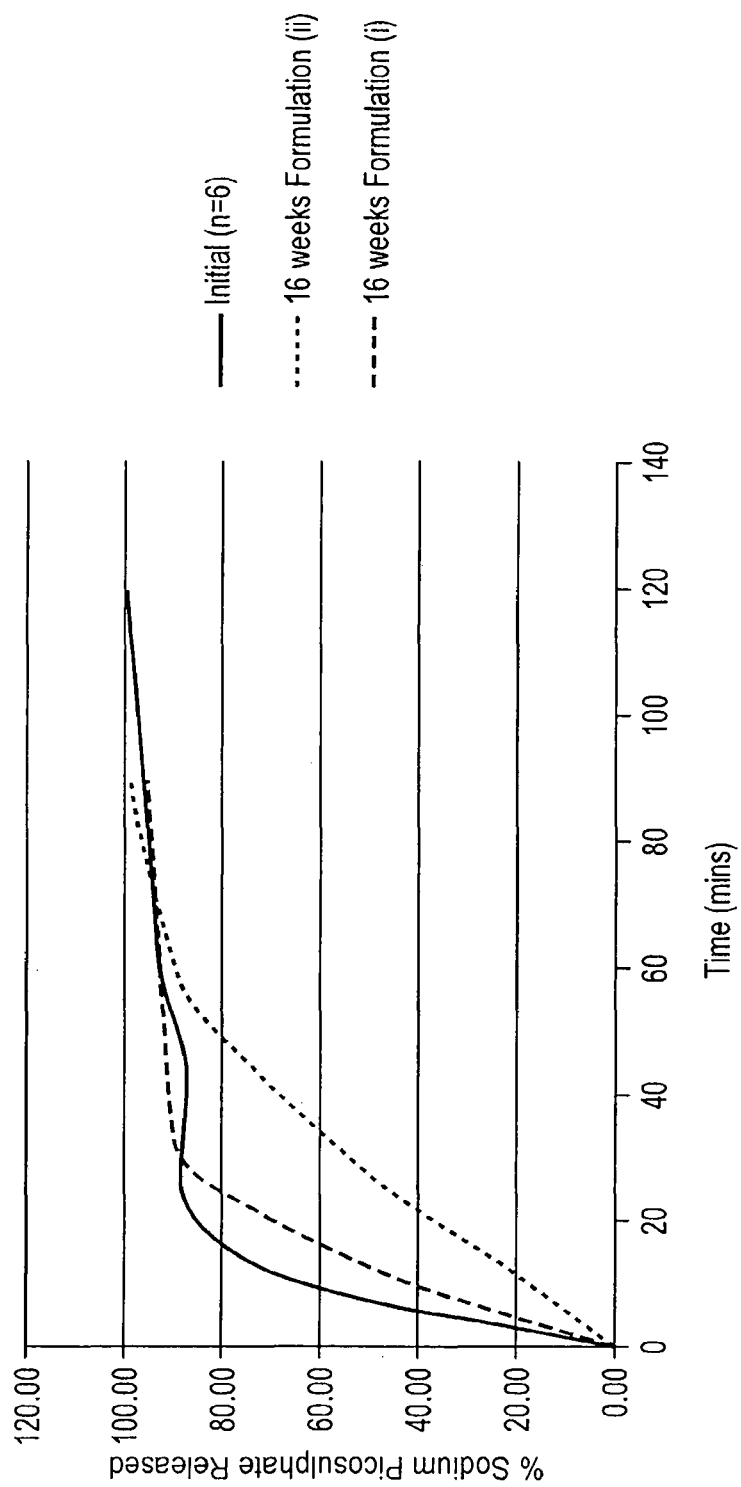
FIG. 1 is a graph showing the release of sodium picosulfate over time from formulations of the present disclosure.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Formulations and methods of manufacturing formulations for use in colonic evacuation are disclosed herein. In an embodiment, a solid dosage formulation includes an intra-granular fraction intermingled with an extra-granular fraction, wherein the intra-granular fraction includes granules comprising at least one osmotic evacuant agent, at least one antacid, and a first pharmaceutically acceptable excipient component, and wherein the extra-granular fraction includes one or more organic acids, a non-metallic lubricating element, and a second pharmaceutically acceptable excipient component.

As used herein, the term "intra-granular fraction" refers to those components of a formulation of the present invention that are within granules.

As used herein, the term "extra-granular fraction" refers to those components of a formulation of the present invention that are outside of the granules. During manufacturing, the extra-granular fraction includes the ingredients that are added to the intra-granular fraction post-drying.

In an embodiment, the intra-granular fraction (i.e. granules) may for example comprise up to 50% of the total weight of the formulation, e.g. from 30% to 50% by weight of the formulation. The at least one osmotic evacuant agent component of the intra-granular fraction may for example comprise up to 1% of the total weight of the formulation. The at least one antacid component of the intra-granular fraction may for example comprise up to 20% of the total weight of the formulation. The first pharmaceutically acceptable excipient component of the intra-granular fraction may for example comprise up to 30% of the total weight of the formulation. The granules of the intra-granular fraction may, for example, have a size of from 25 microns to 1000 microns. The granules of the intra-granular fraction may, for example, have an average size of from 150 microns to 300 microns.

In an embodiment, the extra-granular fraction may for example comprise up to 50% of the total weight of the formulation. The one or more organic acids of the extra-granular fraction may for example comprise up to 40% of the total weight of the formulation. The non-metallic lubricating element of the extra-granular fraction may for example comprise up to 3% of the total weight of the formulation. The second pharmaceutically acceptable excipient component of the extra-granular fraction may for example comprise up to 10% of the total weight of the formulation.

Suitable osmotic evacuant agents include, but are not limited to, sulfate based laxatives and phosphate based laxatives. Examples of sulfate based laxatives include, but are not limited to, sodium picosulfate, sodium sulfate and magnesium sulfate. A mixture of two or more sulfate based laxatives may be used. Examples of phosphate based laxatives include, but are not limited to, sodium dihydrogen phosphate, disodium hydrogen phosphate, sodium biphosphate, sodium acid pyrophosphate, and/or mixtures thereof.

The osmotic evacuant agent may further comprise an antacid selected from the group consisting of magnesium oxide, calcium carbonate, magnesium alginate, magnesium hydroxide, magnesium carbonate, magnesium citrate, magnesium aspartate, and magnesium trisilicate. In an embodiment, the antacid is magnesium oxide. In one embodiment, the osmotic evacuant agent comprises a mixture of sodium picosulfate and magnesium oxide.

In a further embodiment, the sodium picosulfate comprises micronized sodium picosulfate.

The formulation of the present disclosure may be a tablet. For example the tablet may be a compressed tablet, a coated tablet or an exploding tablet. Alternatively, the formulation may comprise a capsule. Examples include a coated capsule or an exploding capsule; a lozenge; or a pill.

The formulation may have a delayed release profile, a slow release profile or a controlled release profile of one or more of the at least one osmotic evacuant agent; the one or more organic acids; or the at least one excipient including a non-metallic lubricating agent.

To achieve a delayed release of one or more components of the pharmaceutical composition, it may be formulated with a coating as noted above. Further, the delayed release of one or more of the components may be achieved by other formulation methods including multiple layers or compartments of the solid oral dosage form.

Suitable organic acids include, but are not limited to, ascorbic acid, citric acid, tartaric acid, mixtures of citric acid and ascorbic acid, and mixtures of tartaric acid in combination with ascorbic acid and/or citric acid.

Typically, the lubricating agent of the formulation comprises a fatty acid ester. For example, the lubricating agent may comprise glyceryl behenate. In an embodiment, Compritol® 888ATO is used as the glyceryl behenate. In another embodiment, the fatty acid ester may result from one or more of the following fatty acids: caprylic acid, capric acid, lauric acid, myristic acid, palmitic acid, stearic acid, lignoceric acid, oleic acid, linoleic acid, erucic acid, linoleic acid, or coconut oil.

The formulation may further include a number of other excipients including a diluent selected from one or a mixture of any one or more of the following: mannitol, lactose monohydrate, microcrystalline cellulose (e.g. sold under the trade name Avicel® PH 101), or sorbitol.

The formulation may further include a binder agent. For example the formulation may include polyvinyl pyrrolidone (PVP), including PVP K30; hydroxypropylcellulose, or polyethylene glycol (PEG), including PEG 10000 or PEG 4000.

Typically, the formulation also includes a stabilizing agent. Suitable stabilizing agents include, but are not limited to, sodium metabisulfite, sodium bisulphite and sodium sulfite.

A disintegrant may also be included in the formulation and may include cross linked povidone (crospovidone). Alternatively sodium starch glycolate (SSG) may be used as a disintegrant.

An anti-foaming agent may also be included in the formulation. Suitable anti-foaming agents include, but are not limited to, polydimethylsiloxane, hydrated silica gel, and mixtures of polydimethylsiloxane and hydrated silica gel. In one embodiment the anti-foaming agent is simethicone. A further example of an anti-foaming agent is dimethicone.

An anti-adherent element may also be included in the formulation for the intra-granular fraction and for the extra-granular fraction and may be the same or different and may comprise one or more (known) substances or compounds which (in appropriate amounts) are capable of reducing the stickiness of the composition or formulation, for example, inhibiting adherence to metal surfaces. Suitable anti-adherent type materials include, but are not limited to, talc and silicon-containing compounds such as colloidal silicon dioxide (e.g. sold under the trade name Aerosil®) as well as mixtures thereof.

Generally, the formulation may be orally administered with any liquid suitable for ingestion. Preferably, water, mineral water, glucose-free mineral water, glucose-free cordial or glucose-free soft drink are used. The volume of liquid consumed with the formulation varies from 250 mL to 2,000 mL, for example, 250 mL to 1,500 mL or 500 mL to 1,500 mL or 2,000 mL.

Generally, the formulation is orally administered to a patient over a period of time. The formulation is usually prepared as a number of tablets or capsules which are taken over a period of time.

A typical total dose of the osmotic evacuant agent is in the range of from 1 to 100 mg, preferably 5 to 50 mg, preferably 10 to 40 mg, more preferably 30 mg. In one embodiment, the evacuant agent in such a dosage regimen comprises a sulfate based laxative.

A typical example of a treatment regimen involves the preparation of the formulation into approximately 30 tablets or capsules. Approximately 5 tablets or capsules are ingested with approximately one glass of liquid over a period of 1 second to 20 minutes, typically 5 seconds to 5 minutes, typically 10 seconds to 3 minutes, typically 30 seconds to 15 minutes, typically 15 minutes to 20 minutes, typically 1 minute to 10 minutes, more typically 1 minute to 6 minutes. A further 5 tablets or capsules are ingested with approximately one glass of liquid over 10 seconds to 20 minutes, typically 30 seconds to 15 minutes, or 15 minutes to 20 minutes, typically 1 minute to 10 minutes, more typically 1 minute to 6 minutes after approximately 20 minutes to 2.5 hours, typically 25 minutes to 1 hour, more typically 30 to 40 minutes. This regimen is repeated until all the tablets or capsules have been ingested.

A typical example of a treatment regimen of the invention involves the preparation of the formulation into approximately 5 to 40 tablets or capsules. Approximately one fifth of the tablets or capsules arc ingested with approximately one glass of liquid over a period of 1 second to 20 minutes, typically 5 seconds to 5 minutes, typically 10 seconds to 3 minutes, typically 30 seconds to 15 minutes, typically 15 minutes to 20 minutes, typically 1 minute to 10 minutes, more typically 1 minute to 6 minutes. A further one fifth of the tablets or capsules are ingested with approximately one glass of liquid over 10 seconds to 20 minutes, typically 30 seconds to 15 minutes, or 15 minutes to 20 minutes, typically 1 minute to 10 minutes, more typically 1 minute to 6 minutes after approximately 20 minutes to 2.5 hours, typically 25 minutes to 1 hour, more typically 30 to 40 minutes. This regimen is repeated until all the tablets or capsules have been ingested.

Generally, the typical examples of the treatment regimen take 2 to 15 hours, for example, 2 to 12 hours or 2.5 to 15 hours, preferably 2.5 to 6.5 hours, more preferably 2 to 4.5 hours, even more typically 2 to 3.5 hours.

If the treatment regimen is administered in two parts, there is usually a difference of 4 to 16 hours, typically 4 to 12 hours, preferably 4 to 8 hours, more preferably 4 to 6 hours, between the administration of the first treatment regimen and the administration of the second treatment regimen.

The formulations of the present disclosure are also useful in the treatment of certain gastrointestinal conditions such as small bowel bacterial overgrowth and irritable bowel syndrome as well as useful in treating acute or chronic bacterial bowel infections, for example, infection of the bowel with one or more bacteria including *Campylobacter jejuni, Yersinia enterocolitica, Clostridium difficile, Clyptosporidium isospora belli*. The formulation of the present disclosure can also be used in the treatment of fungal or viral infections in the bowel. The osmotic colonic evacuant of the present invention can also be used in the treatment of chronic inflammatory bowel disease such as Crohn's disease or ulcerative colitis.

In one embodiment the formulation may be produced by granulation. The granulation steps may include dry granulation. Alternatively, the granulation steps may include wet granulation. The formulation includes an intra-granular fraction intermingled with an extra-granular fraction. Typically, the at least one osmotic evacuant agent is granulated with one or more excipients and dried to provide an initial granulation mixture. As a separate step, the one or more organic acid is added to the initial granulation mixture to provide a second mixture. As a final step one or more lubricating agents may be added to the second mixture and the formulation mixed for a pre-determined time period.

The formulation may further comprise one or more layers or compartments. In this embodiment it is envisaged that the at least one osmotic evacuant agent includes a compound having metallic ions and wherein the compound having metallic ions is in a different layer or compartment to that containing the one or more organic acid. For example, if the at least one osmotic evacuant agent includes magnesium oxide, the formulation in solid dosage form would include the magnesium oxide in a separate layer or compartment to the acid. In an embodiment where ascorbic acid is present, such a physical separation would significantly reduce the degradation of the acid in the presence of metallic cations.

The solid dosage formulation may comprise a coating layer to relatively delay dissolution beyond the mouth of a patient. A suitable coating agent may include PVA, TiO2, talc, lecithin (soy), and xantham gum (e.g. sold under the name Opadry® AMB White). Further, the coating agent may include PVA, polyethylene glycol and talc (sold under the trade name Opadry® II Clear). The coating layer may further include methyl methacrylate and diethylaminoethyl methacrylate copolymer. An example of suitable lubricants is sold under the trade name Kollicoat® and the various compositions are herein incorporated as examples.

EXAMPLES

With aspects of the present formulations and methods now being generally described, these will be more readily understood by reference to the following examples, which are included merely for purposes of illustration of certain features and embodiments of the present formulations and methods and are not intended to be limiting. Table 1 lists the actives and excipients used in the formulation development studies:

TABLE 1

| Material | Trade Name | Supplier |
|---|---|---|
| Sodium picosulfate (micronized) | N/A | Cambrex |
| Simethicone LVA | N/A | Dow Corning |
| Simethicone for DC | N/A | SPI Pharma |
| Magnesium oxide (heavy) | N/A | Intermag |
| Magnesium oxide (granular) | N/A | Intermag |
| EC coated Ascorbic acid | N/A | 3051-W01 |
| FC coated Ascorbic acid | N/A | DSM |
| Sodium ascorbate | N/A | Sigma |
| Mannitol (Pearlitol 200 SD) | Pearlitol ® 200SD | Roquette |
| Lactose monohydrate | Pharmatose ® 200M | DMV Fonterra |
| Microcrystalline Cellulose | Avicel ® PH-101 | FMC |
| Microcrystalline Cellulose | Avicel ® PH-102 | FMC |
| Polyvinyl Pyrrolidone K30 | Povidone K30 | BASF |
| Prosolv Easy Tab | | JRS Pharma |
| Hydroxypropylcellulose (HPC) | Klucel ® | Hercules |
| Polyethylene glycol 10000 | N/A | Clariant |
| Polyethylene glycol 4000 | N/A | Prolabo |
| Citric acid anhydrous | N/A | Sigma |
| Tartaric acid | N/A | Fluka |
| Sodium metabisulphite (97%) | N/A | Alfa Aesar |
| Sodium bisulphite (sodium hydrosulphite) | N/A | Alfa Aesar |
| Sodium sulphite | N/A | Alfa Aesar |
| Sodium starch glycollate | Explotab ® | JRS |
| Crospovidone | Polyplasdone ® XL | ISP |
| Magnesium Stearate | N/A | Riedel de Haen |
| Glyceryl behenate | Compritol ® 888 ATO | Gattefossé |
| Silicon Dioxide | Aerosil ® 200 | In house sample |
| HMPC Capsules | N/A | Qualicaps |
| Sodium Lauryl Sulphate | N/A | VWR |
| OPADRY AMB white | N/A | Colourcon |
| OPADRY II clear | N/A | Colourcon |

Example 1

Formulation Studies

Formulation studies were undertaken to compare powder formulations in capsules (size 0) and tableting studies. Granulation was used as a densification method and various methods such as aqueous, melt and dry granulation were studied. Various changes were made to the formulations and different prototypes prepared. Both the powder blends and the granulated formulations were examined for tapped density, powder flow, compressibility index, moisture content and sieve analysis.

Dry Powder Blends

Powder blends were prepared as follows: the required amounts of active and excipients were dispensed into suitable containers. To a high shear mixer the following were added in order: ascorbic acid (half), MgO (half), SSG, sodium picosulfate, binder, simethicone, MgO (half) and ascorbic acid (half). This mixture was mixed for a predetermined time period, for example, 2 mins at high speed with the mixer shaken/tilted occasionally. Small portions of the powder blend were transferred into a jacketed vessel that was preheated at a selected temperature, for example, 62°

C.-65° C. and mixed with a spatula until granules were formed. This was repeated until all the powder blend was granulated. The granules were emptied into wide opened glass beakers and cooled at room temperature overnight. The granules were sieved, weighed and the extra-granular excipients added accordingly. The resulting mixture was agitated and stirred for a pre-determined time period, for example 10 mins. Lubricant was then added and mixed for a pre-determined time period, for example 1 minute.

Melt Granulation

Melt agglomeration is a process by which the solid fine particles are bound together into agglomerates, by agitation, kneading, and layering, in the presence of a molten binding liquid. Dry agglomerates are obtained as the molten binding liquid solidifies on cooling. The main advantages of the procedure are that neither solvent nor water is used in this process, hence the procedure is suitable for molecules that dissociates in aqueous media. Fewer processing steps are needed thus time consuming drying steps are eliminated. Formulations were prepared using a jacketed vessel and two different hydrophilic meltable binders, PEG 10,000 and PEG 4,000. Both meltable binders were milled down using a Kenwood mixer as they were relatively large flakes. Two methods were used to add the binder to the formulation:

Method A:

The binder was added directly to the formulation blends and mixed either using the low shear mixer (Kenwood) or the Turbula mixer.

Powder blends were prepared as follows:
1. The required amounts of active and excipients were dispensed into suitable containers.
2. The active was then sandwiched between diluent in a high shear mixer (Kenwood) by adding in the following order: ascorbic acid (half), MgO (half), SSG, sodium picosulfate, binder, simethicone, MgO (half) and ascorbic acid (half).
3. Mixed for 2 mins at high speed with the mixer shaken/tilted occasionally.
4. Transfer small portions (40 g) of the powder blend in the jacketed vessel preheated at 62-65° C. mixed with a spatula until granules were formed. This was repeated until all the powder blend was granulated.
5. Emptied the granules in wide opened glass beakers and leave to cool down at room temperature overnight.
6. Sieve, weight and add accordingly the extra-granular excipients.
7. Mix with Turbula mixer for 10 mins at 49 rpm.
8. Add magnesium stearate and mix just for 1 minute at 49 rpm.

Method B:

A single batch of the formulation prepared by hot melt granulation was also prepared by pre-melting the binder in the jacketed vessel, to investigate the effect of the method of the preparation on the flow properties. The other steps were as above.

As the theoretical fill weight for the melt granulation formulation was higher compared to the dry powder blend, it was estimated that formulations with a tapped density of 1.25-1.32 g/ml will be required in order to be filled into size 0 or 0el. Several formulations were prepared where various factors were investigated such as: using different amount and grades of PEG, using different grades of MgO, different mixing time and different temperature for mixing.

As the amount of the meltable binder increased, no significant change in the tapped density was observed. The highest tapped density value achieved was for a formulation containing 10% w/w PEG10,000 mixed for 30 mins at 65° C. Percentages lower than 10% for PEG, might give slightly higher tapped density values to aid packing. Formulations prepared with the same composition but using different grade of MgO (granular and heavy) indicated that a higher tapped density value can be achieved when granular MgO is used. The Can's index was between 13-21%, suggesting that good powder flow was achieved. Formulations prepared with different grade of PEG, gave similar values for the tapped density, but still not high enough to ensure the target fill weight could be achieved. Generally all formulations prepared by hot melt granulation had lower tapped density values than the desired formulation, suggesting that it will be difficult to achieve the target fill weight into a size 0 or 0el.

Using caplet tooling, a tablet was created. Various settings of the tabletting machine were used but the smallest tablets prepared by hand were ~1.1 g (target weigh was 860 mg/caplet for 30 units required). Hence it was decided to increase the fill weight of the caplets and reduce the number of caplets required to deliver the target doses (20 caplets rather than 30). A number of caplets were manually produced using two different machine setting to obtain different hardness and the data indicated that the caplets were uniform in terms of weight and general dimensions. The softer caplets showed a longer disintegration time of just under 14 mins. Hence more super disintegrant will be required in this formulation to reduce the disintegration time. Further, the caplets showed also a change in colour (mottling effect) which might be due to the degradation of one of the excipients during granulation or tab letting.

Direct Compression

A formulation blend was prepared by adding ProSolve® Easy Tab (a commercially available blend containing, MCC 102, $SiO_2$, SSG and sodium stearyl fumarate) and simethicone suitable for direct compression. The theoretical fill weight was increased to allow dosing 24 caplets. The formulation was further optimized by adding 5% Klucel®, Mannitol and increased level of super disintegrant. Caplets were produced in automatic mode using three different settings and results for the tabletting indicated that caplets produced by direct compression were uniform and the hardness varies from 25N (softest) to 78N (hardest), the increase in SSG level reduced the disintegration time, and that all 3 types of caplets, with various hardness's, failed the friability test. The results indicated that this formulation blend was not suitable for tabletting.

Dry Granulation (Slugging)

In a dry granulation process the powder mixture is compressed without the use of heat and solvent. The two basic procedures are to form a compact of material by compression and then to mill the compact to obtain a granules. Two methods are used for dry granulation and slugging is one of these methods. The more widely used method is roller compaction. Granulation by slugging is the process of compressing dry powder of tablet formulation with a tablet press having a die cavity large enough in diameter to fill quickly. Once slugs are produced they are reduced to appropriate granule size for final compression by grinding and sieving or milling. Powder blends were prepared as follows:
1. Required amount of active and excipients were dispensed into suitable containers.

2. Preblend the simethicone with a portion of Avicel® in the high shear blender (Kenwood)
3. The active was then sandwiched between the excipients in Turbula mixer by adding in the following order: ascorbic acid (half), MgO (half), SSG, sodium picosulfate, binder, simethicone/Avicel® mixture from point 2, MgO (half) and ascorbic acid (half)
4. Mix for 10 mins using the Turbula mixer at 49 rpm.
5. Tablet the formulation blend using 15 mm round flat tooling in order to obtain soft tablets.
6. Mill the soft tablets in the mortar and pestles and sieve through 600 gm sieve. Record the weight.
7. Add in sandwich mode the granules and the extra granular excipients and mix in Turbula mixer for 10 mins at 49 rpm.
8. Add magnesium stearate and mix for a further 1 minute at 49 rpm.

Preliminary data on the formulations indicated that a higher amount of super disintegrant was required to aid disintegration. Hence a new formulation was manufactured where:

Simethicone suspension was replaced with simethicone for direct compression to improve uniformity within the blend, Avicel® PH-101 was replaced with grade PH-102 to improve potentially the compressibility of the powder and add increased the level of super disintegrant.

A formulation was tabletted in automatic mode using 2 different machine settings in order to produce caplets with 1000 mg theoretical weight (weight corresponding to 30 caplets required for dosing). Caplets with increased weight were also produced at the hardest setting possible, in order to reduce the number of caplets required for administration. Data indicated that:

Caplets produced were generally uniform and the hardness varied from 61 N (softest) to 99 N (hardest).

Friability tests were performed for all types of caplets. Both sets of caplets failed the friability test as caplets split into halves (delaminate/capping) suggesting that the excipients do not bind well together in the formulations investigated).

These indicated that different types and higher levels of excipients suitable for direct compression were needed it to aid tableting.

Wet Granulation

Wet granulation involves addition of a liquid solution (with or without binder) to powders, to form a wet mass. Typically granules are formed by binding the powder together with help from an adhesive. In the pre-mix step the powders to be granulated and powdered binder are added and mixed prior to the introduction of the aqueous solution. In the wet massing step the components are massed to a predetermined end point. In the drying step the wet mass is dried to a predetermined end point, commonly measured with a test called the loss on drying (LOD). The dried granules are then milled to reduce the size of any caked material into a standardized particle size distribution. Then the final blend is prepared by adding the extra granular excipients, and lubricated. Blends were prepared as follows:

1. Required amount of active and excipients were dispensed into suitable containers.
2. Weight deionized water into a separate container.
3. Place all excipients into the high shear mixer and mix them at high speed for 5 mins
4. Add water gradually and mix continuously until granules were formed.
5. Empty the granules and spread thinly in a tray to dry out either at room temperature (over week-end) or in the oven at −35-40° C.
6. Perform moisture analysis to assess the end time point for drying.
7. Sieve, weigh, add accordingly the extra granular excipients and mix with Turbula mixer for 10 mins at 49 rpm. (sieve analysis was performed for optimized formulations only)
8. Add magnesium stearate and mix just for 1 minute at 49 rpm.

A formulation was tabletted manually using a 19×9 mm caplet tooling using three different machine settings to generate caplets with different hardness'. The caplets were uniform in weight and physical characterization but had a high disintegration time (more than 15 mins for the softest caplets). This suggested that the level of the super disintegrant needed to be increased to reduce the disintegration time to under 15 mins. Thus, a new formulation blend was prepared where lactose was replaced with mannitol (due to a potential Maillard reaction between NH group from sodium picosulfate and lactose) and super disintegrant (SSG) level was increased to improve hardness and disintegration time. Caplets were produced in automatic mode using three different machine setting and the results are shown below:

Caplets produced were uniform in terms of weight and the hardness varies from 64 N (softest) to 133 N (hardest).
The increase in SSG level reduced the disintegration time.
The softest caplets, failed the friability test. The other 2 settings produce caplets which passed both the disintegration and friability test. Conventional compressed tablets that losses less than 0.5% to 1% of weight are considered acceptable.

Following the success in producing caplets (with 1275 mg theoretical weight required for 30 caplets) with good disintegration, friability and dissolution profile, new caplets were produced with increased theoretical weight (1593 mg) in order to reduce the number of caplets administered (24 caplets/patient). Caplets that passed both disintegration and friability test were prepared. However the caplets were thicker and potentially difficult to swallow.

Example 2

Stability Studies

Two formulations were prepared and analyzed, one dry powder blend filled into size Del and one formulation prepared by wet granulation as a caplet.

For the Initial Time Point:
The assay, content uniformity, and dissolution results were variable for the dry blend filled into capsule indicating a non-homogeneous blend of the sodium picosulfate. The water content observed for the capsule formulation was higher than for the tablet formulation.
The assay, content uniformity, and dissolution results were consistent for the wet granulation tablet indicating a homogeneous blend of the sodium picosulfate. Also no impurities were observed in this formulation.

For T=1 Months
The assay, content uniformity, and dissolution results remained variable for the dry blend capsule indicating a non-homogeneous blend of the sodium picosulfate.

The water content observed had increased in comparison to the initial analysis, and remained higher than for the tablet formulation.

The assay, content uniformity, and dissolution results were consistent, and comparable to the initial data, for the wet granulation tablet indicating a homogeneous blend of the sodium picosulfate. The water content observed was consistent in comparison to the initial analysis, and remained to be lower than for the capsule formulation. Also, there was an increase in impurities seen.

Both formulations changed colour at 40° C./75% RH even at T=2 weeks indicating degradation process. It was believed that the browning effect was due to the ascorbic acid degradation in presence of high moisture and on heat.

To confirm which combination of ingredients lead to changing colour of the formulations, several binary and tertiary mixtures of sodium picosulfate, ascorbic acid and citric acid were prepare with the individual excipients present in the formulation. Additional components were added to investigate the effect of adding some stabilizers to the original formulation to prevent browning effect. Samples were also place into three types of containers, closed, opened, and in DUMA bottles with desiccant, to study the effect of the moisture ingress.

Example 3

Excipient Compatibility Studies

Excipient compatibility studies with all excipients against Na picosulfate and ascorbic acid were carried out. Antioxidants like Na meta-bisulphite, Na bisulphite and Na sulphite were added. Further, the study was carried out to determine if citric acid helped stabilize the colour change of ascorbic acid. Samples were assessed at 1 week, 2 weeks, 4 weeks and at 8 weeks.

TABLE 2 lists the study parameters:

| Excipients | Na Picosulfate 10:1 | Ascorbic acid 10:1 | Citric Acid 10:1 |
|---|---|---|---|
| Mannitol | ✓ | ✓ | ✓ |
| Magnesium Oxide powder | ✓ | ✓ | ✓ |
| Simethicone for DC powder | ✓ | ✓ | ✓ |
| Ascorbic acid | ✓ | | ✓ |
| Na starch glycollate | ✓ | ✓ | ✓ |
| PVP K30 | ✓ | ✓ | ✓ |
| HPMC | ✓ | ✓ | ✓ |
| Avicel PH101 | ✓ | ✓ | ✓ |
| Aerosil | ✓ | ✓ | ✓ |
| Mg stearate | ✓ | ✓ | ✓ |
| Compritol 888ATO | ✓ | ✓ | ✓ |
| Na meta-bisulphite | ✓ | ✓ | ✓ |
| Na bisulphite | ✓ | ✓ | ✓ |
| Na sulphite | ✓ | ✓ | ✓ |
| Citric acid | ✓ | ✓ | ✓ |
| Na Picosulfate | | ✓ | |

Tertiary mixtures with components (250 mg MgO+500 mg AA+25 mg Sulphites (or 100 mg Acids)
MgO+ascorbic acid+Na meta-sulphite
MgO+ascorbic acid+Na bisulphite
MgO+ascorbic acid+Na sulphite
MgO+ascorbic acid+citric acid
MgO+ascorbic acid+tartaric acid
MgO+sodium ascorbate+Na meta-sulphite
MgO+sodium ascorbate+Na bisulphite
MgO+sodium ascorbate+Na sulphite
MgO+sodium ascorbate+citric acid
MgO+sodium ascorbate+tartaric acid
Quaternary mixtures with components ((250 m, MgO+500 mg AA+20 mg NaP+25 Sulphites (or 100 mg acids)
MgO+Na picosulfate+ascorbic acid+Na meta-sulphite
MgO+Na picosulfate+ascorbic acid+Na bisulphite
MgO+Na picosulfate+ascorbic acid+Na sulphite
MgO+Na picosulfate+ascorbic acid+citric acid
MgO+Na Picosulfate+ascorbic acid+tartaric acid Binary, tertiary and quaternary mixtures of the API and excipients at various ratios were prepared as follows:
1. Weigh approximately required amount of excipient into a weighing boat.
2. Add approximately half of the excipient quantity into a container.
3. Weigh the API/ascorbic acid/citric acid into the container.
4. Manually mix the blend and with the aid of the micro-spatula break-up any agglomerates.
5. Blend the mixture in a Turbula mixer for 15 minutes at 49 rpm.
6. After mixing all samples were assumed to be homogenous, and were dispensed in suitable containers, then placed on stability storage. Pull times: 1, 2, 4 and 8 weeks. Excipients compatibility study showed that:
    Up to 8 weeks, binary mixtures with ascorbic acid changed colour in presence of excipients and stabilizers containing metallic cations. Some changes were noted also in opened containers also.
    No changes in colour was observed for binary and tertiary mixtures when kept in DUMA bottles with desiccant cap suggesting that the final product will have to be protected from moisture ingress.

The excipient compatibility study of ascorbic acid with various excipients indicated that ascorbic acid degrades in the presence of metallic cations (such as: $Cu^{2+}$, $Fe^{3+}$, $Zn^{2+}$). As a result, two changes were made to the formulation blend prepared by wet granulation. Firstly, the sodium starch glycollate was replaced with crospovidone XL, and secondly the magnesium stearate was replaced with Compritol 888ATO. Also the Avicel® PH101 was added split 50/50 intra-granular and extra-granular.

Example 4

Optimization of Wet Granulated Formulation Blend

Further optimization studies were carried out for the wet granulated formulation. To reduce ascorbic acid degradation in the presence of metallic cations, some excipients of the formulation containing metallic cations were replaced with non-metallic excipients. Additionally, and with a view to further minimising ascorbic acid degradation, the steps of granulation were modified and the effects of having a coating reviewed.

Three wet granulation formulations were prepared, where Avicel was added i) intra granular, ii) split intra granular and extra granular and iii) extra granular only. All three batches were prepared as follows:
1. Required amount of active and excipients were dispensed into suitable containers.
2. Weight deionized water into a separate container.
3. Place all excipients into the high shear mixer and mix at high speed for 2 mins.

4. Add water gradually and mix continuously until granules were formed. Record the amount of water used and the mixing time.
5. Empty the granules and spread thinly in a tray to dry out either at room temperature 3 (over week-end) or in the oven at –35-40° C.
6. Perform moisture analysis to assess the end time point for drying.
7. Collect approximately 100 g of the dry granules and perform sieve analysis.
8. Add accordingly the extra granular excipients and mix with Turbula mixer for 10 rains at 49 rpm.

Sieve analysis indicated that:
Formulations containing Avicel as intra-granular excipient (100 or 50%) have a smaller median particle diameter compared to the formulation containing no Avicel intra-granular. This suggests that the formulations containing some Avicel intra-granular are more suitable for further studies, as bigger granules might lead to segregation caused by particle size difference between materials in a bulk blend.
Powder flow properties indicated that all three formulations prepared had good powder flow properties.

Example 5

Formulations

Formulation A was prepared by wet granulation at –1.5 kg scale, yielding enough batch to prepare between 25 and 30 tablets, wherein all the tablets combined yield a total dose of about 30 mg sodium picosulfate, about 7 g of magnesium oxide, about 15 g of ascorbic acid, and about 100 mg of simethicone. Table 3 lists the components of Formulation A:

TABLE 3

| Intra-granular Components | Weight (mg) | Weight (mg) | Wt/unit | % w/w | Weight (g) |
|---|---|---|---|---|---|
| Mannitol | 7200 | 7200.00 | 240.00 | 18.82 | 301.17 |
| Magnesium Oxide granules | 7000 | 7000.00 | 233.33 | 13.30 | 292.81 |
| Sodium picosulfate (micronized) | 30 | 31.17 | 1.04 | 0.08 | 1.30 |
| Simethicone for DC | 100 | 147.71 | 4.92 | 0.39 | 6.18 |
| Crospovidone | 940 | 940.00 | 31.33 | 2.46 | 39.32 |
| PVP K30 | 1800 | 1800.00 | 60.00 | 4.71 | 75.29 |
| Microcrystalline Cellulose-50% (Avicel® PH101) | 1893 | 1893.00 | 63.10 | 4.95 | 79.18 |
| The above constituents were granulated and dried then sieved and the following added accordingly: Extra-granular Components | | | | | |
| Microcrystalline Cellulose-50% (Avicel® PH101) | 1893 | 1893.00 | 63.10 | 4.95 | 79.18 |
| Ascorbic acid | 15000 | 15151.52 | 505.05 | 39.61 | 633.78 |
| Crospovidone | 940 | 940.00 | 31.33 | 2.46 | 39.32 |
| Aerosil® | 105 | 105.00 | 3.50 | 0.27 | 4.39 |
| The above constituents were granulated and dried then sieved and the following added accordingly: | | | | | |
| Compritol® 888ATO | 1149 | 1149.00 | 38.30 | 3.00 | 48.06 |
| TOTAL | 38157 | 38250.40 | 1275.01 | 100.00 | 1600.00 |

Median Particle Diameter for the intra-granular granules of Formulation A was 289 microns.

Formulation B was prepared by wet granulation at –1.5 kg scale, yielding enough batch to prepare between 25 and 30 tablets, wherein all the tablets combined yield a total dose of about 30 mg sodium picosulfate, about 7 g of magnesium oxide, about 15 g of ascorbic acid, and about 100 mg of simethicone. Table 4 lists the components of Formulation B:

TABLE 4

| Intra-granular Components | Weight (mg) | Weight (mg) | Wt/unit | % w/w | Weight (g) |
|---|---|---|---|---|---|
| Mannitol | 6314.5 | 6314.50 | 210.48 | 16.51 | 247.63 |
| Magnesium Oxide granules | 7000 | 7000.00 | 233.33 | 18.30 | 274.51 |
| Sodium picosulfate (micronized) | 30 | 31.17 | 1.04 | 0.08 | 1.22 |
| Simethicone for DC | 100 | 147.71 | 4.92 | 0.39 | 5.79 |
| Crospovidone | 1925 | 1925.00 | 64.17 | 5.03 | 75.49 |
| PVP K30 | 1100 | 1100.00 | 36.67 | 2.88 | 43.14 |
| Microcrystalline Cellulose-50% (Avicel® PH101) | 1700 | 1700.00 | 56.67 | 4.44 | 66.67 |
| The above constituents were granulated and dried then sieved and the following added accordingly: Extra-granular Components | | | | | |
| Microcrystalline Cellulose-50% (Avicel® PH 101) | 1700 | 1700.00 | 56.67 | 4.44 | 66.67 |
| Ascorbic acid | 15000 | 15151.52 | 505.05 | 39.61 | 594.18 |
| Crospovidone | 1925 | 1925.00 | 64.17 | 5.03 | 75.49 |
| Aerosil® | 105 | 105.00 | 3.50 | 0.27 | 4.12 |
| The above constituents were granulated and dried then sieved and the following added accordingly: | | | | | |
| Compritole 888ATO | 1150 | 1150.00 | 38.33 | 3.01 | 45.10 |
| TOTAL | 38157 | 38249.90 | 1275.00 | 100.00 | 1500.00 |

Median Particle Diameter for the intra-granular granules of Formulation B was 175 microns.

The blend and content uniformity of uncoated batches of Formulation A were found to be consistent and to a high standard, see Table 5 below.

TABLE 5

| | Uncoated Tablets | |
|---|---|---|
| | Blend uniformity | Content uniformity |
| Batch | % Assay | % Assay |
| Min | 83.41 | 86.74 |
| Max | 108.61 | 100.42 |
| Avg | 90.71 | 91.44 |
| S.D | 7.95 | 4.62 |
| % RSD | 8.77 | 5.05 |

The appearances of the tablets were initially smooth, plain colour on all sides and free from any spots. Further studies to compare uncoated tablets of Formulation A with coated tablets were performed. Tablet characteristics of uncoated batches of Formulation A are provided below in Table 6:

TABLE 6

| | | | Uncoated Tablets | | | | |
|---|---|---|---|---|---|---|---|
| Tablet | Weight (g) | Length (mm) | Thickness (mm) | Width (mm) | Hardness (N) | Friability test | Disintegration time |
| Average | 1.28 | 19.24 | 6.83 | 9.12 | 106.40 | PASSED (0.16%) | PASSED (5-6 MIN) |
| Std | 0.01 | 0.09 | 0.06 | 0.01 | 2.15 | | |
| % RSD | 0.74 | 0.49 | 0.86 | 0.15 | 2.02 | | |

Further samples of Formulation A using different coatings and coating parameters were prepared. Examples of the coatings used in the studies are listed in Table 7:

TABLE 7

| Coating Type | Chemical Composition of Coating layer | Coating Solution Concentration | Coating parameters | Coating Weight gain |
|---|---|---|---|---|
| Opadry ® AMB White | PVA, TiO2, talc, lecithin(soy), Xanthan gum | 20% w/w | Time 37 min Temp 46-50° C. | 4.85% w/w |
| Opadry ® II Clear | PVA, polyethylene glycol, talc | 20% w/w | Time 19 min Temp 46-50° C. | 4.62% w/w |

The coated formulations of Formulation A were:

Coated Formulation (i)=Formulation A coated using Opadry® AMB White and stored at 25° C./60% R1-1;

Coated Formulation (ii)=Formulation A coated using Opadry® AMB White and stored at 40° C./75% R1-1

Coated Formulation (iii)=Formulation A coated using Opadry® II clear at 40° C./75% R1-1.

A stability study of the coated tablets was undertaken and the following results observed:
Appearance of the tablet initially and after 4 weeks.
A) Initial appearance:
  Coated Formulation (i)
  oblong, smooth, plain white colour on both sides, free from any spots
  Coated Formulation (ii)
  oblong, smooth, plain white colour on both sides, free from any spots
  Coated Formulation (iii)
  not tested
B) Appearance at 4 weeks:
  Coated Formulation (i)
  oblong, smooth, plain white colour on both sides, free from any spots
  Coated Formulation (ii)
  oblong, smooth, plain white colour on both sides, free from any spots
  Coated Formulation (iii)
  oblong, smooth, pale yellow colour on both sides
Moisture Content of the Tablets after 4 Weeks.

Table 8 shows the % Water Content by Karl Fischer (T=4 weeks) for three different batches of each of coated formulations (i), (ii) and (iii).

TABLE 8

| Batch | Coated Formulation (i) | Coated Formulation (ii) | Coated Formulation (iii) |
|---|---|---|---|
| 1 | 6.01 | 7.08 | 6.15 |
| 2 | 6.52 | 6.87 | 6.11 |
| 3 | 5.94 | 6.96 | 6.34 |
| Mean | 6.15 | 6.97 | 6.20 |

Table 9 shows the Moisture Content by Karl Fischer (comparative data of mean % water content of each coated formulation at T=0, 2 weeks, 4 weeks, 8 weeks, 12 weeks and 16 weeks).

TABLE 9

| Formulation | Initial | 2 weeks | 4 weeks | 8 weeks | 12 weeks | 16 weeks |
|---|---|---|---|---|---|---|
| (i) | 7.67 | 7.78 | 6.15 | 6.60 | 6.48 | 6.49 |
| (ii) | 7.67 | 7.60 | 6.97 | 6.59 | 6.76 | 7.68 |

Drug Release

Formulations (i) and (ii) were further tested for drug release of the sodium picosulfate over time. Table 10 lists the dissolution parameters

TABLE 10

| Dissolution Parameters | |
|---|---|
| Media | 1% SLS (Sodium Lauryl Sulphate) in de-ionised water |
| RPM | 100 (150 from 60 to 90 minutes) |
| Bath temperature | 37.5 ± 0.5° C. |
| Volume | 500 ml |
| Apparatus | USP-11 (paddle) |
| Time points | 0, 10, 20, 30, 45, 60 and 90 mins |

Figure 2:
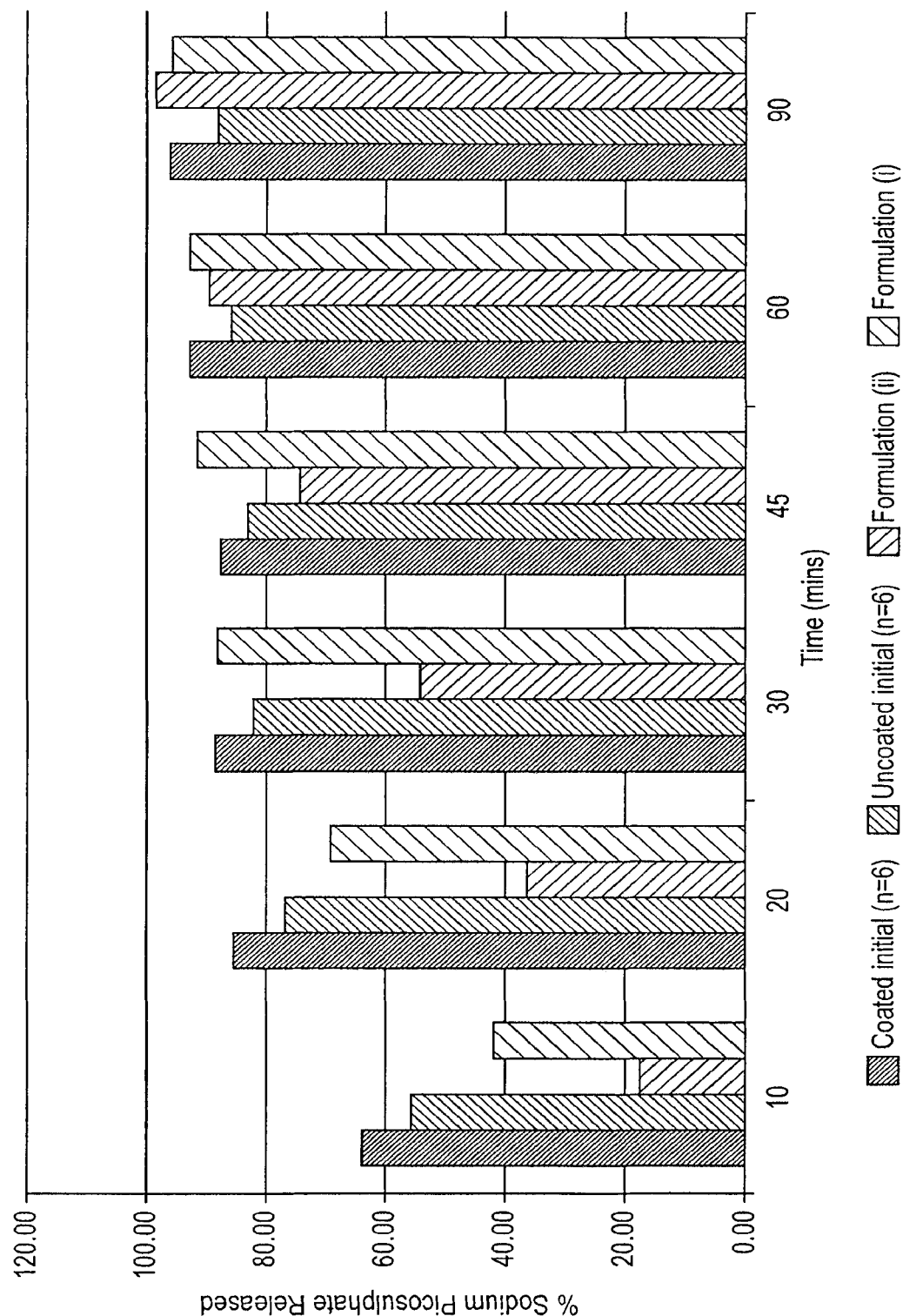
FIG. 2 is a bar graph showing the release of sodium picosulfate over time from formulations of the present disclosure.

Percentage drug release of sodium picosulfate in formulations (i) and (ii) over time is shown in FIG. 1 and FIG. 2.

SUMMARY

At 16 weeks, there was no change in the physical appearance of the tablets of formulation (ii) compared to initial samples. There was also no significant variation observed in the moisture level from the initial samples to the 16 week samples.

The dissolution data showed that 80% drug release was achieved after 30 minutes for the tablet of formulation (i). A delay in the release of sodium picosulfate was observed for formulation (ii), that is, when kept at 40° C. at 75% RH.

The formulation of this disclosure provided a stable tablet form with no signs of degradation at 16 weeks and which delivered an optimal drug release profile.

All patents, patent applications, and published references cited herein are hereby incorporated by reference in their entirety. It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive. Various presently unforseen or unanticipated alternatives, modifications, variations, or improvements therein may be subsequently made by those skilled in the art which are also intended to be encompassed by the following claims.

What is claimed is:

1. A preparation for cleansing of a colon, the preparation comprising:
 a plurality of coated tablets housed in at least one container, the coated tablets sufficiently designed to delay dissolution of a tablet beyond the mouth of a user after oral administration, wherein each tablet comprises all of the following ingredients: sodium picosulfate, magnesium oxide and an organic acid,
  wherein each tablet comprises intragranular excipients and extragranular excipients,
  wherein the intragranular excipients include microcrystalline cellulose and crospovidone, and excludes sodium starch glycolate, and
  wherein the extragranular excipients include microcrystalline cellulose and crospovidone, and excludes sodium starch glycolate and magnesium stearate, wherein all of the tablets together provide a total of 30 mg sodium picosulfate, 7 g of magnesium oxide, and 15 g of an organic acid.

2. The preparation of claim 1, wherein the organic acid is one of ascorbic acid, citric acid, tartaric acid, or combinations thereof.

3. The preparation of claim 1, wherein the organic acid is ascorbic acid.

4. The preparation of claim 1 comprising from 5 tablets to 40 tablets.

5. The preparation of claim 1, comprising at least 25 tablets.

6. The preparation of claim 1, comprising approximately 30 tablets.

7. The preparation of claim 1, wherein the cleansing of the colon is to prep a user for a colonoscopy.

8. The preparation of claim 1, wherein the at least one container includes a desiccant.

9. The preparation of claim 1, wherein the sodium picosulfate is micronized.

10. A method of evacuating a colon of a patient comprising orally administering to the patient, within a 24-hour time frame, the preparation of claim 1.

* * * * *